United States Patent
Konen et al.

[11] Patent Number: 6,135,946
[45] Date of Patent: Oct. 24, 2000

[54] METHOD AND SYSTEM FOR IMAGE-GUIDED INTERVENTIONAL ENDOSCOPIC PROCEDURES

[75] Inventors: Wolfgang Konen; Martin Scholz, both of Bochum, Germany

[73] Assignee: U.S. Philips Corporation, New York, N.Y.

[21] Appl. No.: 09/102,479

[22] Filed: Jun. 22, 1998

[30] Foreign Application Priority Data

Jun. 23, 1997 [EP] European Pat. Off. ............. 97201922

[51] Int. Cl.⁷ ........................................ A61B 1/04
[52] U.S. Cl. ................................. 600/117; 600/407
[58] Field of Search ................................. 600/117, 118, 600/102, 109, 160, 921, 407, 425, 427, 476; 606/130

[56] References Cited

U.S. PATENT DOCUMENTS

| | | |
|---|---|---|
| 4,722,056 | 1/1988 | Roberts et al. |
| 4,922,909 | 5/1990 | Little et al. ............................. 600/300 |
| 5,249,581 | 10/1993 | Horbal et al. ............................ 600/407 |
| 5,261,404 | 11/1993 | Mick et al. ............................... 600/425 |
| 5,273,039 | 12/1993 | Fujiwara et al. ........................ 600/407 |
| 5,389,101 | 2/1995 | Heilbrun et al. |
| 5,409,001 | 4/1995 | Seyler et al. ............................. 600/407 |
| 5,515,160 | 5/1996 | Schulz et al. ............................ 600/117 |
| 5,622,170 | 4/1997 | Schulz ..................................... 600/407 |
| 5,638,819 | 6/1997 | Manuwaring et al. ................. 600/117 |
| 5,704,897 | 1/1998 | Truppe ..................................... 600/117 |
| 5,711,299 | 1/1998 | Manuwaring et al. ................. 600/117 |
| 5,749,362 | 5/1998 | Funda et al. ............................. 600/407 |
| 5,776,050 | 7/1998 | Chen et al. ............................... 600/117 |

FOREIGN PATENT DOCUMENTS

WO9403100  2/1994  WIPO.

*Primary Examiner*—John P. Leubecker
*Attorney, Agent, or Firm*—Dwight H. Renfrew

[57] ABSTRACT

An image guided surgery system comprises an endoscope (11) with an image pick-up apparatus and a posi ion measuring system (10,21) for measuring the position of the endoscope (11). A data processor (2) is arranged to process image data according to the measured position of the endoscope and derive updated image data from the processed image data and imae information from the image pick-up apparatus. The processed image data are derived from said image data and said image information from the image pick-up apparatus and said measured position. For example the image data are CT or MRI images or the image data represents one or several anatomical landmarks in the body of a patient (12) to be examined.

5 Claims, 1 Drawing Sheet

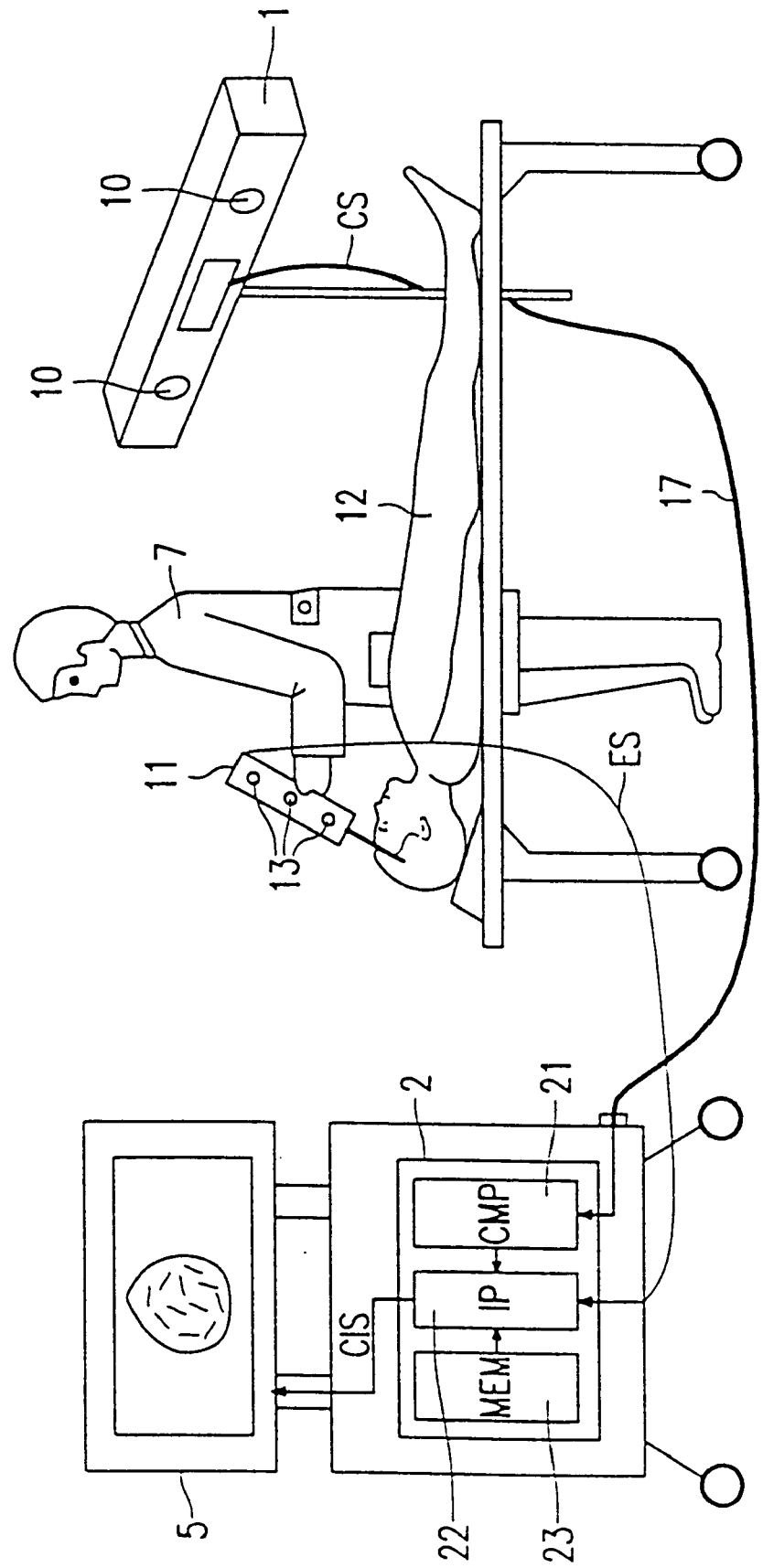

METHOD AND SYSTEM FOR IMAGE-GUIDED INTERVENTIONAL ENDOSCOPIC PROCEDURES

BACKGROUND OF THE INVENTION

1. Field of the Invention

The invention relate to an image guided surgery system.

2. Description of Related Art

Such an image-guided surgery system is known from the U.S. Pat. No. 5,389,101.

An image-guided surgery system is used to show a surgeon the position of a surgical instrument in an operating zone in the body of the patient during surgery. The known image-guided surgery system comprises a position measuring system for measuring the position of the surgical instrument. Prior to surgery, images (for example, CT or MRI images) are made of the patient. During surgery the position measuring system measures the position of the surical instrument relative to the patient. The image guided surgery system is provided with a computer which calculates the position in such a pre-recorded image which corresponds to the measured position of the surgical instrument. The pre-recorded image is displayed on a monitor and the actual position of the surgical instrument is indicated therein. The surgeon can see where the surgical instrument is situated in the operating zone by observing the image displayed on the monitor, without the surgeon having a direct view thereof. The image on the monitor reveals how the surgeon can move the surgical instrument in the operating one without a serious risk of unnecessarily damaging tissues and notably without a risk of damaging vital organs.

An image-guided surgery system of this kind is preferably used in neurosurgery for showing the surgeon exactly where the surgical instrument is situated in the brain during cerebral surgery.

The position measuring system measures the position of the surgical instrument by recording ages of the surgical instrument from different directions by means of two cameras. The position measuring system also measures the position of the patient. Thus, the cameras supply image signals that represent the position of the surgical instrument and the position of the patient. The data processor derives the position of the surgical instrument relative to the patient during surgery from image signals from the individual cameras and from the positions of the cameras relative to one another.

Often, the surgical instrument is an endoscope. The term endoscope is used hereinafter to designate a surgical instrument that is suitable to be entered into the body of a patient to be examined and which provides visual information, e.g. in the form of an image or a view, of the interior of patient's anatomy. During surgery, it may occur that the endoscope cannot function properly, in particular because it cannot supply appropriate visual information.

SUMMARY OF THE INVENTION

An object of be invention is to provide an image guided surgery system which substantially improves the application possibilities for use of an endoscope in interventional and/or surgical operations.

This object is achieved according to the invention by an image guided surgery system comprising:

an endoscope with an age pick-up apparatus for receiving image information of a region to be examined.

a position measuring system for measuring the position and/or orientation of the endoscope relative to the region to be examined and a data processor arranged to
  receive image data relating to the region to be examined
  transform the image data according to the measured position and/or orientation of the endoscope to derive combined image data from the image information from the image pick-up apparatus and the transformed imaged data.

The image data relate to a portion of the patient's anatomy that is investigated by means of the endoscope. In particular, the image data are generated prior to the operation by another imaging modalty such as an x-ray CT scanner, an MRI system or an ultra-sound system. The image guide surgery system according to the invention achieves that during the operation both actual image information from the endoscope as well as image data from another source are available. The endoscope is arranged so as to provide image information of the interior of the patient's anatomy. To that end the endoscope is provided with an image pick-up apparatus such as an electronic (miniature) videocamera, or the image pick-up apparatus is an optical system such as a system of lenses and optical fibres. By means of such an optical system the user of the endoscope can view the interior of the patient. The image information from the endoscope can thus be directly viewed or it can be represented by an image signal such as an electronic videosignal generated by the videocamera. The image information receive the image pick-up apparatus is generated during the examination of the patient with the end scope, i.e. during the interventional procedure. The image information includes pictures containing information about a region in the field of view of the image pick-up apparatus, such as a set of images of the region to be examined in the patient's anatomy. The image data on the other hand are generated separately from the interventional procedure or instance the image data include images, such as CT or MRI images, generated prior to the intervention or the image data includes positions of a number of anatomical landmarks or separate markers in the patient's anatomy. The combined image information includes simultaneously or successively the images from the image pick-up apparatus and the image data, so that the image data add useful information to the image information. Thus, the invention in particular achieves that an image of the region around the actual position of the endoscope, especially the region around a distal end of the endoscope, can be displayed in comination with the image as generated by the endoscope. In particular for the event that the image information from the endoscope is deteriorated or even useless because e.g. the view of the image pick-up apparatus is partially or completely blocked, the transformed image data are displayed together with or instead of the image information from the endoscope so that the operator is able to safely maneuver the endoscope in the patient's body while there is no reliable image from the image pick-up apparatus available.

The combination of the image information from the endoscope and the processed image data makes it easier to have the endoscope in the patient's body without serious risk of damaging tissue. Especially when the view of the endoscope's image pick-up apparatus is blocked e.g. by fluids or by a bend in the patient's anatomy, the processed image data provide adequate information. Moreover, the combined image data for example relate to a transformed image derived from the image data, such as a transformed CT or MRI image, and the image information from the endoscope. These image data are transformed on the basis of the measured position of the endoscope so that the transformed image data represent an image corresponding the image picked-up by the image pick-up apparatus of the endoscope. The transformed image e.g. CT or MRI image is displayed together with the image information from the endoscope or the transformed image e.g. CT or MRI image and the image information the endoscope are displayed alternatingly or the rendition of transformed image data temporarily replaces the rendition of the image information from the endoscope.

For example, when the image information from the endoscope is not adequate, for instance because the view of the image pick-up apparatus is blocked due to bleeding or a bend in the patient's anatomy, the image information from the endoscope is replaced by the corresponding transformed image e.g. CT of MRI image. In such a situation the endoscope cannot be moved safely inside the patient's body on the basis of the information from the endoscope, but the transformed image data, such as the transformed CT or MRI image, provides adequate information enabling the endoscope to be safely moved, for example so as to remove the endoscope from the bleeding area.

Furthermore, the processed image data can be selected so as to relate to a next position of the endoscope when a movement of the endoscope is intended. Thus it is achieved that the user can see if the intended motion of the endoscope is safe.

Moreover, the image information from the endoscope can be advantageously used to update the image data. That is, the transformed image data can not only involve pre-recorded images e.g. CT or MRI images, but also updated images e.g. CT or MRI images can be used. To that end, the trasformed image data are derived from said image data, said image information from the image pick-up apparatus and said measured position and/or orientation of the endoscope.

In particular, anatomical landmarks are observed by means of the endoscope and their actual positions are determined. Notably, these actual positions are measured with the help of the position measuring system. For example, the distal end of the endoscope is placed successively at the anatomical landmarks in the patient's body and the position measuring system measures the position of the endoscope at those anatomical landmarks. These actual positions are compared with the corresponding positions of the images of the landmarks in the image data, e.g. CT or MRI images so as to detect a tissue displacement in the patient's anatomy. Such tissue displacement can occur, for example, due to draining of fluid or the removal or reduction of tumour tissue. The updated image data are derived from the image data and the tissue displacement. The updated image data include the image data taking the tissue displacement into account.

It is noted that in the article Vision based navigation system for an endoscope in Image and vision computing 14(1996)763–772 by G. N. Kahn and D. F. Gillies, an endoscope is disclosed in which image information from the endoscope is recorded and the recorded image information is used when the actual view of the endoscope is not adequate. However, the known endoscope is not employed together with a position measuring system.

A preferred embodiment of an image guided surgery system according to the invention is provided with a display unit. By means of the image signal the combined image data are rendered visible on the display unit. Thus, on the display unit the image information from the endoscope is shown together with an e.g. a CT or MRI image, or the image information from the endoscope is shown alternatingly with the CT or MRI image. In particular, when the view of the endoscope is obstructed e.g. due to bleeding or a bend in the patient's anatomy, the image data e.g. CT or MRI images are displayed on the display unit. The display unit is for example a monitor comprising a cathode-ray tube or a liquid crystal screen. The display unit can also be arranged so as to display image information from the endoscope simultaneously with the transformed image data. For example, the image information from the endoscope and the transformed image e.g. CT or MRI images can be displayed in separate portions of the display unit, or one over the other. Further, particular anatomical landmarks in the image information from the endoscope can be displayed in the rendition of the transformed image which is e.g. a CT or MRI image.

A preferred embodiment of an image guided surgery system according to the invention is provided with writeable memory unit. The stored combined image data are suitable for documentation of the intervention and later reference. For example, the stored combined image data can be retrieved later so as to compare the patient's anatomy before and after the intervention and/or some lime after the intervention.

In a preferred embodiment of an image guided surgery system according to the invention the image data are generated by the image pick-up apparatus of the endoscope. Several images from the endoscope can be assembled so as to enlarge the effective field of view of the endoscope. Such an assembled image enables the user of the endoscope to move the endoscope very accurately and safely. Such an assembled image is also an effective tool for making a diagnosis. Preferably, the assembled image is simply made by fusing separate images from the endoscope. When fusing separate images, the successive positions of the endoscope when it picks-up the images are taken into account. Notably, in this way it is achieved that the separate images are fused appropriately so as to yield an assembled image that hardly contains perturbations and/or artefacts caused by the assembling.

In a preferred embodiment of an image guided surgery system according to the invention the data processor is arranged to detect a change of the image information from the endoscope. When a change is detected in the image information from the endoscope but the measured position of the endoscope is unchanged, it may well be possible that a part of the endoscope has become detached. Thus, by detecting such a situation it is adequately detected that e.g. loosening of the endoscope has become detached or loosened from its holder. The image guided surgery system e.g. provides a warning signal at the moment such a dangerous situation occurs. Such a warning signal is derived from a difference between the change of the image information and the change of the position of the endoscope. If the endoscope is held in a fixed position, e.g. by means of a stand, then a change of the image information is useful to detect that a part of the endoscope has become detached.

The invention also relates to a method of examining a region in the patient's anatomy by means of an endoscope. The method according to the invention comprising the steps of receiving image information from the region to be examined by means of the endoscope measuring the position and/or orientation of the endoscope relative to the region to be examined receiving image data relating to the region to be examined transforming the image data according to the measured position and/or orientation and deriving combined image information from the image pick-up apparatus and the transformed image data. It is noted the method according to the invention provides a technical feature in the form of the combined image which is useful to assist the operator to maneuver the endoscope safely inside the patient's body.

As elaborated with respect to the image-guided surgery apparatus the method according to the invention enables the operator to safely maneuver the endoscope in the patient's body when there is no reliable image from the image pick-up apparatus available.

BRIEF DESCRIPTION OF THE DRAWINGS

These and other aspect of the invention will be elucidated with reference to the embodiments described hereinafter and with reference to the accompanying drawing wherein The Figure illustrates an image guided surgery system according to the invention.

DETAILED DESCRIPTION OF THE PREFERRED EMBODIMENT

The Figure shows a schematic diagram of an image guided surgery system according to the invention. The image guide surgery system comprises a position measuring system 1,2 which includes a camera unit 1 with one or more cameras 10 and a dataprocessor 2. The one or several cameras pick-up ages from different directions of the endoscope 11 and derive electronic camera signals (CS) representing the images picked up by the cameras. For example, the camera unit 1 incorporates two CCD image sensors mounted on a rigid frame. The frame is moveable as to direct the CCD sensors to the operating region. The camera signals from separate cameras, or subsequent image signals from the single camera but from successive camera positions are supplied to the dataprocessor 2. To that end the camera unit 10 is coupled to the dataprocessor 2 by way of a cable 17. The dataprocessor 2 includes a computer 21 which, on the basis of the image signals, computes the position of the endoscope relative to the patient 12 who is undergoing a surgical operation. The image processor 22 is incorporated in the dataprocessor 2. The endoscope is fitted with light or infrared emitting diodes 13 (LEDs or IREDs) which emit radiation for which the cameras 10 are sensitive. The computer 21 also computes the corresponding position of the endoscope 11 in an earlier generated image such as a CT image or an MRI image. The CT data and/or MRI data are stored in a memory unit 23.

In the image data fiducial markers are imaged which are placed on particular positions on the patient. For example laad or MR susceptible markers are placed at the ears, nose and forehead of the patient. At the start of the operation the fiducial markers are indicated with the endoscope or with a separate pointing instrument and their positions in space are measured by the position measuring system. The computer 21 calculates the transformation matrix which connects the positions in space of the fiducial markers to the corresponding positions of the images of the markers in the earlier generated image. This transformation matrix is subsequently use d to compute a corresponding position in the image for a position in space in the actual operating region.

The image data from the memory unit 23 are applied to the image processor 22. The position-data computed by the computer 21 are also supplied to the image processor 22. The computer 21 may be alternatively programmed to calculate the co-ordinates of the position of the endoscope with respect to a fixed reference system, then the image processor 22 is arranged to convert those coordinates to the corresponding position in the image. The image processor is further arranged to select an appropriate set of image data on the basis of the position of the endoscope. Such an appropriate set e.g. represents CT or MRI image data of a particular slice through the operating region.

The endoscope 11 is provided with a miniature videocamera which is not visible in the Figure because it is mounted on the distal end of the endoscope which is inside the patient. The miniature videocamera picks-up image information of the interior of the patient's anatomy. The miniature videocamera derives the endoscope signal (ES) that represents the image information and supplies the endoscope signal (ES) to the dataprocessor, notably to the image processor 22. In particular the endoscope signal is an electronic videosignal of which the signal levels represent brightness values of the image picked-up by the miniature videocamera. The image processor 22 generates a combined image signal (CIS) which combines the earlier generated image data with the endoscope signal from the endoscope. For example, the combine image signal represents the image data and the image information from the endoscope. In particular, with the combined image signal is employed to display the image of the interior o the patient picked-up by the endoscope and corresponding image data from the memory 23. Notably, a CT or MRI image corresponding to the image from the endoscope are shown in overlay, next to one another or one after the other.

As an alternative, the image data from the memory are processed so as to represent an image corresponding to the image picked-up by the endoscope's image pick-up apparatus and are represented in the direct view of the endoscope. In this alternative the image pick-up includes an optical system by means of which the physician can observe the interior of the patient at the distal end of the endoscope. The processed image data are e.g. displayed on a display and by means of further optics mixed with the direct view. Such optics for mixing the displayed image wit a direct view is known per se from the international application WO 95/25979.

The image formed fr m by combination of image information from the endoscope and the image data from the metory is displayed on the display device 5. The display device is e.g. a monitor comprising a athode-ray tube, but an LCD display screen may be used as well.

We claim:

1. A method of examining a region interior to a patient during an interventional procedure by means of an endoscope provided with an image pick-up apparatus comprising:

recieving image data generated separately from the interventional procedure and relating to the region to be examined, recieving image information from the region to be examined by means of the image pick-up apparatus of the endoscope, updating the image data by taking into account tissue displacements, tissue displacements being derived by comparing imaging positions of anatomic landmarks in the recieved image data with measured positions of the anatomic landmarks in the region, measuring the position and/or orientation of the endoscope relative to the region to be examined, transforming the updated image data according to the measured position and/or orientation of the endoscope so that the transformed updated image information, and deriving combined image information from the image pick-up apparatus and the transformed-updated image data.

2. The method of claim 1, further comprising a step of displaying the combined image data, wherein said displaying comprises displaying images from the received image information simultaneously or successively with images from the transformed updated image data.

3. An image guided surgery system for performing an interventional procedure in a region interior to a patient comprising:

means for providing image data generated separately from the interventional procedure and relating to the region to be examined, an endoscope with an image pick-up apparatus for providing image information from the region, a position measuring system for measuring the position of the endoscope, and data processor means, the data processor means being responsive to the provided image data, the provided image information, and the measured position of the endoscope, the data processor means for updating the provided image data by taking into account tissue displacements, tissue displacements being derived by comparing image positions of anatomic landmarks in the provided image data with measured positions of the endoscope when placed at the actual positions of the anatomic landmarks in the region, transforming the updated image data according to the measured position and/or orientation of the endoscope so that the transformed updated image data represent images corresponding to the received image information, and deriving combined image information from the image pick-up apparatus and the transformed-updated image data.

4. The system of claim 3, further comprising a display device for displaying the derived combined image information.

5. An image guided surgery system for performing an interventional procedure in a region interior to a patient comprising:

an endoscope with an image pick-up apparatus for providing image information from the region, a position measuring system for measuring the position of the endoscope, and data processor means, the data processor means being responsive to the provided image information and to the measured position of the endoscope, the data processor means for detecting a change of the provided image information without a change of the measured position of the endoscope and for providing a warning signal.

* * * * *